(12) United States Patent
Fisher et al.

(10) Patent No.: US 7,138,495 B2
(45) Date of Patent: Nov. 21, 2006

(54) HUMAN PHOSPHODIESTERASE IV ISOZYMES

(75) Inventors: Douglas A. Fisher, Mystic, CT (US); Michael D. Robbins, East Lyme, CT (US)

(73) Assignee: Pfizer Inc., New York, NY (US)

( * ) Notice: Subject to any disclaimer, the term of this patent is extended or adjusted under 35 U.S.C. 154(b) by 161 days.

(21) Appl. No.: 10/703,939

(22) Filed: Nov. 7, 2003

(65) Prior Publication Data

US 2004/0073019 A1 Apr. 15, 2004

Related U.S. Application Data

(60) Division of application No. 10/165,135, filed on Jun. 6, 2002, now Pat. No. 6,914,133, which is a division of application No. 09/717,953, filed on Nov. 21, 2000, now Pat. No. 6,489,457, which is a continuation of application No. 08/472,600, filed on Jun. 7, 1995, now Pat. No. 6,323,041, which is a continuation of application No. 08/432,327, filed on May 1, 1995, now abandoned, which is a continuation of application No. 08/075,450, filed on Jun. 11, 1993, now abandoned.

(51) Int. Cl.
*C07K 1/00* (2006.01)
(52) U.S. Cl. .................................................. 530/350
(58) Field of Classification Search ................ 530/350, 530/300
See application file for complete search history.

(56) References Cited

U.S. PATENT DOCUMENTS

| 5,527,896 A | 6/1996 | Wigler et al. ............... 536/23.5 |
| 5,631,286 A | 5/1997 | Christensen, IV et al. .. 514/520 |
| 6,323,041 B1 | 11/2001 | Fisher et al. ................. 436/501 |

OTHER PUBLICATIONS

Colicelli et al (Proc. Natl. Acad. Sci. (1989) 86:3599-3603).*
Davis et al., Proc. Natl. Acad. Sci (USA), May 1989, 86: 3604-3608.
Kurihara et al., Biochem. Biophys. Res. Comm, Aug. 1990, 170(3): 1074-1081.
Livi et al., Mol. Cell Biol., Jun. 1990, 10(6): 2678-2686.
Torphy et al., J. Biol. Chem., Jan. 1992, 267(3): 1798-1804.
McLaughlin et al., J. Biol. Chem. 268(9): 6470-6476.
McHale et all, Molecular Pharmacology, 39: 109-113.

* cited by examiner

*Primary Examiner*—Jeffrey Fredman
(74) *Attorney, Agent, or Firm*—Gregg C. Benson; Nicholas I. Slepchuk

(57) ABSTRACT

This invention relates to novel nucleic acid sequences encoding three novel human phosphodiesterase (hPDE IV) isozymes. It also relates to polypeptides encoded by such sequences.

This invention also relates to an assay method for detecting the presence of such novel isozymes in human cells, and to a method of identifying compounds or other substances that inhibit or modify the activity of such isozymes.

10 Claims, 5 Drawing Sheets

FIG. 2A

```
B1-644   ..........................................................TGGATGGTGAAAGC -631
         ***      M  T  A  K  D  S  S  K  E  L  T  A  S  E  P  E  V  C  I  K  T  F  K  E
-204
B1-630   TAGCACTCCTTACAAGATATGACAGCAAAAGATTCTTCAAAGGAACTACTGCTTCTGAACCTGAGTTTGCATAAAGACTTTCAAGGAG -541

-180     Q  M  H  L  E  L  P  R  L  P  G  N  R  P  T  S  P  K  I  S  P  R  S  S  P  R  N  S
B1-540   CAAATGCATTTAGAACTTGAGCTTCCGAGATTACCAGGAAACAGACCTACATCTCCTAAAATTTCTCCACGCAGTTCACCAAGGAACTCA -451

-150     P  C  F  F  R  K  L  L  V  N  K  S  I  R  Q  R  R  R  F  T  V  A  H  T  C  F  D  V  E  N
B1-450   CCATGCTTTTTCAGAAAAGTTGCTGGTGAATAAAGCATTCGGCAGCGTCGTGCTTCACTGTGGCTCATACATGCTTTGATGTGGAAAAT -361

-120     G  P  S  P  G  R  S  P  L  D  P  Q  A  S  S  S  A  G  L  V  L  H  A  T  F  P  G  H  S  Q
B1-360   GGCCCTTCCCCAGGTCGGAGTCCCACTGGATCCCCAGGCCAGCTCTTCCGCTGGGCTGTACTTCACGCCACCTTTCCTGGGCACAGCCAG -271

B2-336   ..........................................................CATTTATGCAGATGAGCTTATAAGAGACCGTTCCCTCCGCCTTCTTCCTCAGAGGAAGTTTCTGG -271

-90      R  R  E  S  F  L  Y  R  S  D  S  D  Y  D  L  S  P  K  A  M  S  R  N  S  S  L  P  S  E  Q
B1-270   CGCAGAGAGTCATTCTCTACAGATCAGACAGCGACTATGACTTGTCACCAAAGGCGATGTCGAGAAACTCTTCTCTTCCAAGCGAGCAA -181
         ***
B2-270   TAGATCACCGACACCTCATCCAGGCGGGGGGTTGGGGGAAACTGGCACCAGCATCCCAGGCAGAGCACCACCACTGTGATTTGTTCTCCT -181

-60      H  G  D  D  L  I  V  T  P  F  A  Q  V  L  A  S  L  R  S  V  R  N  N  F  T  I  L  T  N  L
B1-180   CACGGCGATGACTTGATTGTAACTCCTTTTGCCCAGGTCCTTGCCAGCTTGAGAAACAACTTCACTATACTGACAAACCTT -91
-47                                               M  K  E  H  G  G  T  F  S  S  T  G  I  S  G  S
B2-180   GGTGAGAGAGCTGAAGGAAGGAGCCAGCGTCCAAATAATGAAGGAGCACGGGGGCACCTTCAGTAGCACCGGAATCAGCGGTGGTAGC -91
                                                                                            ***
B3-135   ...........................................................GTGGAAGCAAACAGCGGAGGCAAGGGGTTGTTTCGGACACACTAG -91

-30      H  G  T  S  N  K  R  S  P  A  A  S  Q  P  P  V  S  R  V  N  P  Q  E  E  S  Y  Q  K  L  A
B1 -90   CATGGTACATCTAACAAGAGAGTCCCCAGCTAGTCCCTGTCTCCAGAGTCAACCCACAAG AAGAATCTTATCAAAAATTAGCA -1
-30      G  D  S  A  M  D  S  L  Q  P  L  Q  P  N  Y  M  P  V  C  L  F  A  E  E  S  Y  Q  K  L  A
B2 -90   GGTGACTCTGCTATGGACTCTCTGCAGCCTCGACAGCCTCCAGCCTCCAGCCTCAACTACATGCCTGTGTTGTTTGCAG AAGAATCTTATCAAAAATTAGCA -1

B3 -90   AGAGTAAGTCAGAGAATCTTCGTGTTGAGGCAGCATTGCAAAATTGAAGATGAAGAAGGAAG AAGAATCTTATCAAAAATTAGCA -1
```

```
hPDE IV-B1    V  S  R  V  N  P  Q  E     E  S  Y  Q  K  L  A  M  E  T
              GTCTCCAGAGTCAACCCACAAG     AAGAATCTTATCAAAAATTAGCAATGGAAACG hPDE IV-B2    M  P  V  C  L  F  A  E     E  S  Y  Q  K  L  A  M  E  T
              ATGCCTGTGTGTTTGTTTGCAG     AAGAATCTTATCAAAAATTAGCAATGGAAACG hPDE IV-B3    GAAGATGAAGAAAGGAAGGAAG                                M  E  T
                                         AAGAATCTTATCAAAAATTAGCAATGGAAACG
                    |          |               |         |       |  |
                   -40        -30             -20       -10     -1  1
                                     ↑
                                Splice Junction
```

```
hPDE IV-B1:   MTAKDSSKEL TASEPEVCIK TFKEQMHLEL ELPRLPGNRP TSPKISPRSS PRNSPCFFRK  60 hPDE IV-B1:   LLVNKSIRQR RRFTVAHTCF DVENGPSPGR SPLDPQASSS AGLVLHATFP GHSQRRESFL  120 hPDE IV-B1:   YRSDSDYDLS PKAMSRNSSL PSEQHGDDLI VTPFAQVLAS LRSVRNNFTI LTNLHGTSNK  180
Rat DPD:      .......... .......... .......... ........MKE --I------L -----AP---
hPDE IV-B2:   .......... .......... .......... .......... HGGTFSSTG- SGGSGDSAMD
hPDE IV-B3:   .......... .......... .......... .......... .......... .[*RVSQRI hPDE IV-B1:   RSPAASQPPV SRVNPQEESYQKLA METLEE LDWCLDQLET IQTYRSVSEM ASNKFKRMLN  240
Rat DPD:      ------A--- T--SL----- ---------- ---------- ---------- ----------
hPDE IV-B2:   SLQPLQPNYM PVCLFA----
hPDE IV-B3:   FVLRQHCKIE DEERKE-----]

hPDE IV-B(all): RELTHLSEMS RSGNQVSEYI SNTFLDKQND VEIPSPTQKD REKKKQQLM TQISGVKKLM  300
Rat DPD:        ---------- ---------- ---------- ---------- ---------- ---------- hPDE IV-B(all): HSSSLNNTSI SRFGVNTENE DHLAKELEDL NKWGLNIFNV AGYSHNRPLT CIMYAIFQER  360
Rat DPD:        ---------- ---------- ---------- ---------- ---------- ---------- hPDE IV-B(all): DLLKTFRISS DTFITYMMTL EDHYHSDVAY HNSLHAADVA QSTHVLLSTP ALDAVFTDLE  420
Rat DPD:        ----K----- ---V------ ---------- ---------- ---------- ---------- hPDE IV-B(all): ILAAIFAAAI HDVDHPGVSN QFLINTNSEL ALMYNDESVL ENHHLAVGFK LLQGEHCDIF  480
Rat DPD:        ---------- ---------- ---------- ---------- ---------- -----E---- hPDE IV-B(all): MNLTKKQRQT LRKMVIDMVL ATDMSKHMSL LADLKTMVET KKVTSSGVLL LDNYTDRIQV  540
Rat DPD:        Q--------- ---------- ---------- ---------- ---------- ---------- hPDE IV-B(all): LRNMVHCADL SNPTKSLELY RQWTDRLMEE FFQQGDKERE RGMEISPMCD KHTASVEKSQ  600
Rat DPD:        ---------- ---------- ---------- ---------- ---------- ---------- hPDE IV-B(all): VGFIDYIVHP LWETWADLVQ PDAQDILDTL EDNRNWYQSM IPQSPSPPLD EQNRDCQGLM  660
Rat DPD:        ---------- ---------- ---------- ---------- ---------- --RS------ hPDE IV-B(all): EKFQFELTLD EEDSEGPEKE GEGHSYFSST KTLCVIDPEN RDSLGETDID IATEDKSPVD  720
Rat DPD:        ---------E ---------- ---PD----- ---------- ---------E ------LI-- hPDE IV-B(all): T  721
Rat DPD:
```

HUMAN PHOSPHODIESTERASE IV ISOZYMES

CROSS REFERENCE TO RELATED APPLICATIONS

This is a division of U.S. application Ser. No. 10/165,135, filed Jun. 6, 2002 now U.S. Pat. No. 6,914,133 entitled "Human Phosphodiesterase IV Isozymes" which is a division of U.S. application Ser. No. 09/717,953, filed Nov. 21, 2000 now U.S. Pat. No. 6,489,457 which is continuation of Ser. No. 08/472,600 filed Jun. 7, 1995 which has issued as U.S. Pat. No. 6,323,041, which is a continuation of U.S. application Ser. No. 08/432,327 filed May 1, 1995 which is abandoned, which is a continuation of U.S. application Ser. No. 08/075,450, filed Jun. 11, 1993 which is abandoned.

BACKGROUND OF THE INVENTION

This invention relates to novel nucleic acid sequences encoding three novel human phosphodiesterase IV (hPDE IV) isozymes.

Cyclic nucleotide phosphodiesterases (PDE's) are a family of enzymes that catalyze the degradation of cyclic nucleotides. Cyclic nucleotides, particularly cAMP, are important intracellular second messengers, and PDEs are one cellular component that regulates their concentration. In recent years, five PDE enzymes (PDE I–PDE V), as well as many subtypes of these enzymes, have been defined based on substrat affinity and cofactor requirements (Beavo J A and Reifsnyder D H, *Trends Pharmacol. Sci.* 11:150 [1990]; Beavo J, in: *Cyclic Nucleotide Phosphodiesterases: Structure, Regulation and Drug Action*. Beavo J and Housley M D (Eds.). Wiley: Chichester, pp. 3–15 [1990]).

Theophylline, a general PDE inhibitor, has been widely used in the treatment of asthma. It has been speculated that selective inhibitors of PDE isozymes and their subtypes (particularly the cAMP-specific PDE IV) will lead to more effective therapy with fewer side effects (for reviews, see Wieshaar RE et al., *J. Med. Chem.*, 28:537 [1985] and Giembycz M A, *Biochem. Pharm.*, 43:2041 [1992], Lowe J A and Cheng J B, *Drugs of the Future*, 17:799–807 [1992]). However, even PDE IV selective drugs such as rolipram suffer from emetic side effects that limit their use. An even more selective approach is to inhibit individual subtypes of PDE IV, each one of which is expected to have its own tissue distribution. If the PDE IV isozyme responsible for efficacy is different from that causing side effects, an isozyme selective drug could separat therapeutic and side effects. The cloning and expression of the human PDE IVs would greatly aid the discovery of isozyme-selective inhibitors by providing purified isoenzymes to incorporate into drug assays.

Mammalian PDE IV, the homologue of the Drosophila Dunce gene (Chen C N et al., *Proc. Nat. Acad. Sci.* (USA) 83:9313 [1986]), is known to have four isoforms in the rat (Swinnen J V et al., *Proc. Nat. Acad. Sci.* (USA) 86:5325 [1989]). The cloning of one human isoform of PDE IV from monocytes was reported in 1990 (Uvi GP et al., *Mol. Cell. Bio.*, 10:2678 [1990]). From Southern blot data, the authors concluded that this enzyme was probably the only PDE IV gene in humans, with the possible exception of one other isozyme. The same group has recently published the sequence of a second human isoform isolated from brain that they designate hPDE IV-B to distinguish it from the monocyte form, which they designate as hPDE IV-A (McLaughlin MM et al., *J. Biol. Chem.* 268:6470 [1993]). For clarity, we will use this nomenclature as well.

Our invention relates to the nucleic acid sequences encoding three novel human PDE IV isozymes generated by differential splicing from a single gene. We designate these isoforms as hPDE IV-B1, hPDE IV-B2 and hPDE IV-B3. The hPDE IV-B2 sequence encodes a polypeptide nearly identical to that reported for hPDE IV-B (McLaughlin MM et al., *J. Biol. Chem.* 268:6470 [1993]), and the hPOE IV-B2 splice variant represents the unspliced genomic sequence with respect to the differential splice site. Of the two other splice variants, hPDE IV-B1 encodes the longest polypeptide chain, as well as the N-terminal sequence homologous to its rat homologue, DPD (Colicelli J, et al., *Proc. Nat. Acad. Sci.* (USA) 86:3599 [1989]).

The novel human PDE IV DNA sequences and their encoded peptides may be used to screen for drugs that are selective for a particular human PDE IV isozyme. Such novel DNA sequences may also be used in assays to detect the presence of a particular POE IV isozyme in human cell lines, thus providing information regarding th tissue distribution of each isozyme and its biological relevance with respect to particular disease states.

The following abbreviations are used throughout this patent:

| | |
|---|---|
| BAL | bronchoalveolar lavage |
| bp | base pair(s) |
| cAMP | cyclic adenosine 3',5'-monophosphate |
| dNTP | 2'-deoxynucleoside-5'-triphosphate |
| dATP | 2'-deoxyadenosine-5'-triphosphate |
| dCTP | 2'-deoxycytidine-5'-triphosphate |
| dGTP | 2'-deoxyguanidine-5'-triphosphate |
| dTTP | 2'-deoxythymidine-5'-triphosphate |
| hPDE IV-A | human monocyte PDE IV |
| hPDE IV-B | human brain PDE IV |
| hPDE IV-B1 | human brain PDE IV, splice variant 1 |
| hPDE IV-B2 | human brain PDE IV, splice variant 2 |
| hPDE IV-B3 | human brain PDE IV, splice variant 3 |
| kb | kilobase(s) |
| PCR | polymerase chain reaction |
| PDE | cyclic nucleotide phosphodiesterase |
| PDE I | $Ca^{2+}$/Calmodulin-dependent PDE |
| PDE II | cGMP stimulated PDE |
| PDE III | cGMP inhibited PDE |
| PDE IV | high affinity cAMP-specific PDE |
| PDE V | cGMP specific PDE |
| RACE | Rapid Amplification of cDNA Ends |
| RT | avian myeloblastosis virus (AMV) reverse transcriptase |
| RT-PCR | PCR of RT-transcribed mRNA |
| SSC | 1X SSC = 0.15 M NaCl, 0.015 $Na_3$ citrate pH 7.0 |

The nucleotides and amino acids represented in the various sequences contained herein have their usual single letter designations used routinely in the art.

SUMMARY OF THE INVENTION

This invention relates to novel nucleic acid sequences encoding the novel hPDE IV isozymes hPDE IV-B1, hPDE IV-B2 and hPDE IV-B3. More specifically, it relates to DNA segments comprising, respectively, the DNA sequences of SEQUENCE ID NO. 1, SEQUENCE ID NO. 2 and SEQUENCE ID NO. 3, as defined below, or alleleic variations of such sequences. It also relates to polypeptides produced by expression in a host cell into which has been incorporated one of the foregoing DNA sequences or an alleleic variation of such sequence.

This invention also relates to an isolated polypeptide comprising the amino acid sequence of SEQUENCE ID NO. 4, SEQUENCE ID NO. 5 or SEQUENCE ID NO. 6.

This invention also relates to recombinant DNA comprising the DNA sequence of SEQUENCE ID NO. 1, SEQUENCE ID NO. 2 or SEQUENCE ID NO. 3, or an alleleic variations of such sequence.

This invention also relates to an isolated DNA segment comprising the genomic promoter region that regulates transcription or translation of the DNA sequence of SEQUENCE ID NO. 1, SEQUENCE ID NO. 2 or SEQUENCE ID NO. 3, or an alleleic variation of such sequence.

This invention also relates to an assay method for detecting the presence of hPDE IV-B1, hPDE IV-B2 or hPDE IV-B3 in human cells, comprising: (a) performing a reverse transcriptase-polymerase chain reaction on total RNA from such cells using a pair of polymerase chain reaction primers that are specific for, respectively, hPDE IV-B1, hPDE IV-B2 or hPDE IV-B3, as determined from, respectively: (i) the DNA sequence of SEQUENCE ID NO. 1 or an alleleic variation thereof; (ii) th DNA sequence of SEQUENCE ID NO. 2 or an alleleic variation thereof; or (iii) the DNA sequence of SEQUENCE ID NO. 3 or an alleleic variation thereof; and (b) assaying the appearance of an appropriately sized PCR fragment by agarose gel electrophoresis.

This invention also relates to a method of identifying compounds or other substances that inhibit or modify the activity of hPDE IV-B1, hPDE IV-B2 or hPDE IV-B3, comprising measuring the activity of, respectively, hPDE IV-B1, hPDE IV-B2 or hPDE IV-B3, in: (a) a cell line into which has been incorporated recombinant DNA comprising the DNA sequence of SEQUENCE ID NO. 1, SEQUENCE ID NO. 2 or SEQUENCE ID NO. 3, or an alleleic variation thereof, or (b) a cell line that naturally selectively expresses hPDE IV-B1, hPDE IV-B2 or hPDE IV-B3, as determined by the assay method described above.

This invention also relates to an isolated DNA segment comprising a DNA sequence that is a subset of SEQUENCE ID NO. 1, SEQUENCE ID NO. 2 or SEQUENCE ID NO. 3, or an alleleic variation thereof, and that is capable of hybridizing to, respectively, SEQUENCE ID NO. 1, SEQUENCE ID NO. 2 or SEQUENCE ID NO. 3, or an alleleic variation thereof, when used as a probe, or of amplifying all or part of such sequence when used as a polymerase chain reaction primer.

As used herein, the term "functionally equivalent DNA segment" refers to a DNA segment that encodes a polypeptide having an activity that is substantially the same as the activity of the polypeptide encoded by the DNA to which such segment is said to be functionally equivalent.

As used herein, the term "subset of a DNA sequence" refers to a nucleotide sequence that is contained in and represents part, but not all of such DNA sequence, and is sufficient to render it specific to such sequence when used as a PCR primer and to render it capable of hybridizing to such sequence when used as a probe at high stringency.

The term "functionally equivalent polypeptide" refers to a polypeptide that has substantially the same activity as the polypeptide to which it is said to be functionally equivalent.

The term "subset of a polypeptide" refers to a peptide sequence that is contained in and represents part, but not all of such polypeptide.

BRIEF DESCRIPTION OF THE DRAWINGS

FIG. 2. hPDE IV-B1, hPDE IV-B2 and hPDE IV-B3 DNA and Translated Amino Acid Sequences. (+) Numbering begins with the "A" of the ATG start codon in hPDE IV-B3. Four stop codons are designated by "***". These include the protein translation stop (1,552), and the stop codons that prevent the coding region from coritinuing further in the 5' direction in each splice variant: hPDE IV-B1 (−630), hPDE IV-B2 (−270) and hPDE IV-B3 (−89). The alternate splice junction is between nucleotides −23 and −24, and the putative splice acceptor sequence in hPDE IV-B2 (−33 to −24) is underlined.

FIG. 3. Alternative Splice Junction. This figure is a close-up view of the splice junction between −24 and −23, showing the three aligned sequences hPDE IV-B1, hPDE IV-B2 and hPDE IV-B3. The putative splice acceptor sequence in hPDE IV-B2 (−33 to −24) is underlined.

FIG. 4. Amino Acid Sequence Comparison: hPDE IV-B1, hPDE IV-B2, hPDE IV-B3, and Rat DPD. Identity with the hPDE IV-B1 sequence is indicated with a dash. A translation of the region upstream of the hPDE IV-B3 start codon is shown in parenthesis to highlight the complete sequence divergence of hPDE IV-B2 and hPDE IV-B3 from hPDE IV-B1 at amino acid 196.

FIG. 5. Restriction Map of the hPDE IV-B Genomic Locus. Transcriptional orientation (5'–3') of hPDE IV-B is from left to right, with the approximate positions of exons known by partial sequence analysis indicated by solid boxes (coding). The position of the stop codon is indicated by an asterisk, followed by a segment of a 3' untranslated region (open box). Regions hybridizing strongly to the 308 bp probe, as described in the text, are indicated by a dark hatched box, while weakly hybridizing regions are shown as lighter hatched regions. It is because of weak hybridization between the EcoRI and HindIII sites in λ11.1 that we position an exon (with a "?") in that interval. The hybridizing restriction fragments seen in genomic blots with the 308 bp probe are indicated below the figure.

DETAILED DESCRIPTION OF THE INVENTION

Figure 1:
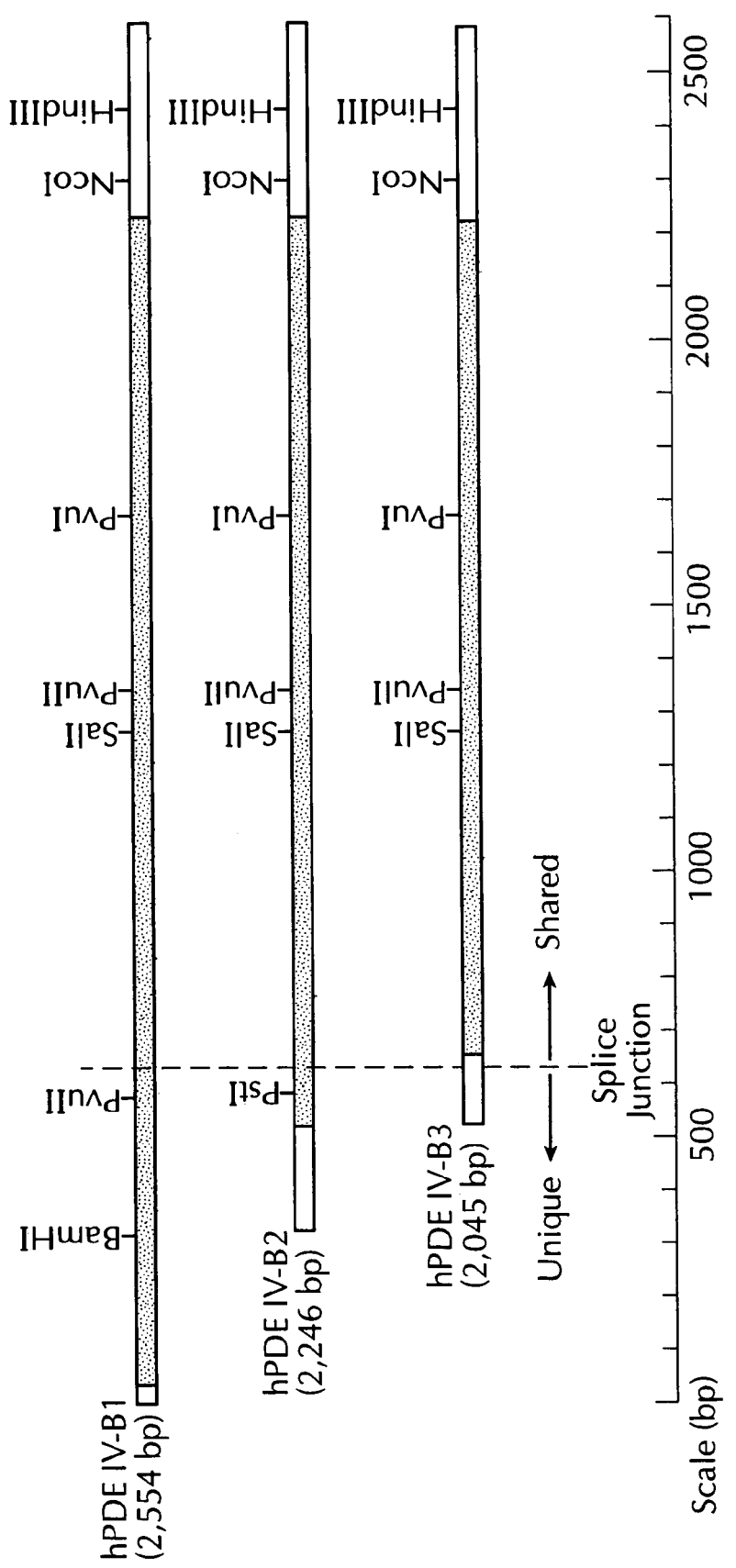
FIG. 1. hPDE IV-B1, hPDE IV-B2 and hPDE IV-B3 Restriction MaD and Clone Diagram. This figure shows the relationship between the cDNA sequences encoding the three splice variants. Black boxes indicate protein coding regions and open boxes indicate untranslated regions.

The procedures by which the DNA sequences encoding for novel isozymes hPDE IV-B1, hPDE IV-B2 and hPDE IV-B3 were identified and isolated as described below.

Discovery of PDE IV-B Using Degenerate PCR: The degenerate PCR primers (5'-Deg and 3'-Deg, as described below in the section labelled Materials and Methods) were designed against amino acid sequences that were conserved (with one exception) between the six published PDE IV sequences from human, rat, and Drosophila (Uvi GP et al., *Mol. Cell. Biol.* 10:2678 [1990], Swinnen J V et al., *Proc. Nat. Acad. Sci.* (USA) 86:5325 [1989], and Chen C N et al., *Proc. Nat. Acad. Sci.* (USA) 83:9313 [1986]). These primers were expected to amplify 308 bp of PDE IV sequence from any human isoform mRNA that also conserved those amino acids. The RT-PCR was done on human BAL sample total RNA as described below in the section labelled Materials and Methods, and a fragment of the correct size was obtained. Sequence analysis of this fragment showed it to be different from hPDE IV-A (Uvi GR et al., [1990]). This fragment of hPDE IV-B corresponds to bp 1,575 to 1,882 in SEQUENCE ID NO. 1. This fragment was isolated from several independent PCR reactions and sequenced to confirm that no apparent differences were due to PCR artifacts.

Isolation of a cDNA Clone for hPDE IV-B: The human medulla cDNA library was screened as described below in the section labelled in Materials and Methods, and a single cDNA clone was obtained. The insert sequence corresponds to bp 924 to 2,554 of SEQUENCE ID NO. 1, and was clearly not full length in the coding region by comparison with the known PDE IV sequences. Also, since no polyA tract was found at the 3' end of this clone, we do not believe that the 3' untranslated region is complete however, this is of no functional significance with respect to producing a hPDE protein. There was one nucleotide difference between the cDNA sequence and the PCR fragment sequence. SEQUENCE ID NO. 1 contains a C at bp 1792, the nucleotide seen in the cDNA sequence, rather than the T that has been seen at this position in PCR isolations. We believe that this difference, which changes an amino acid, is real, and represents an alleleic difference in the human population.

Figure 2B:
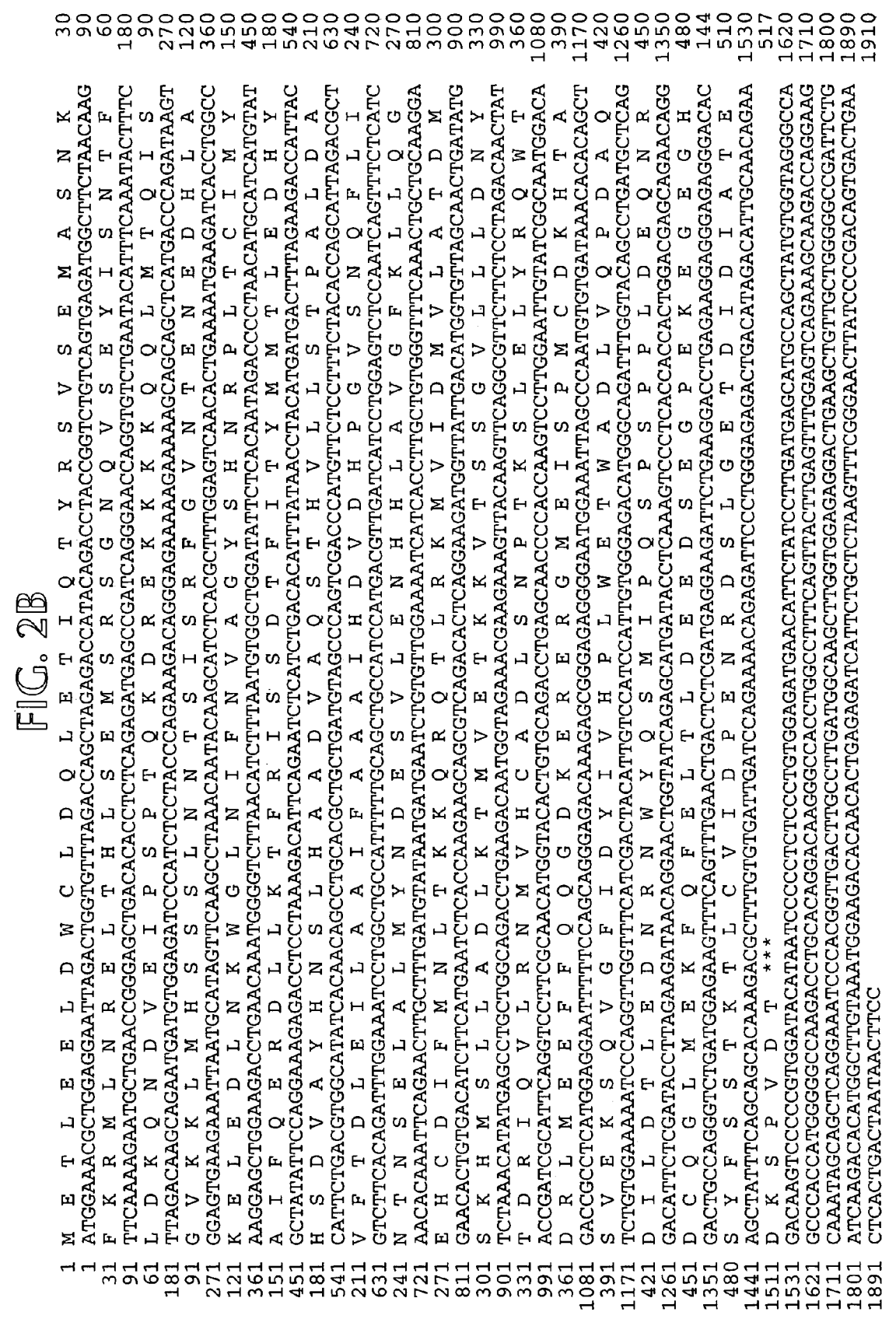

Completion of the cDNA Sequence using the RACE Method: The RACE method showed that there was not just a single 5' end to the hPDE IV-B cDNA, but at least three. Fragments of different sizes were obtained, all beginning at the GSi oligonucleotide primer site and extending towards the 5' end of the cDNA. The three fragments that were successfully sequenced had a variable length of non-homologous sequence at the 5' end that joins the hPDE IV sequence at the same point in all three cases. These different 5' ends, when joined to the rest of the cDNA sequence, make three forms of the hPDE IV-B gene that we designate hPDE IV-B1 (SEQUENCE ID NO. 1), hPDE IV-B2 (SEQUENCE ID NO. 2), and hPDE IV-B3 (SEQUENCE ID NO. 3). The three hPDE IV-B isoforms make polypeptides of different lengths. From the cDNA sequences, hPDE IV-B1 is predicted to encode a protein of 721 amino acids (SEQUENCE ID NO. 4), hPDE IV-B2 a protein of 564 amino acids (SEQUENCE ID NO. 5), and hPDE IV-B3 a protein of 517 amino acids (SEQUENCE ID NO. 6). The three isoforms are shown diagrammatically in FIG. 1, and the DNA sequence and amino acid translation of the three isoforms of hPDE IV-B is shown in FIG. 2.

The most logical explanation for the three hPDE IV-B isoforms is that they are generated by alternative splicing of 5' exons onto the shared 3' sequence. The putative alternative splice junction is shown at −23 bp in FIG. 2. To test this hypothesis, w amplified PCR fragments from human genomic DNA using primers on either side of the putative splice junction. hPDE IV-B1 and hPDE IV-B3 specific 5' primers did not give amplified fragments, indicating that the sequences on either side of the putative splice lie further than 2 kb apart in genomic DNA (the practical limit for PCR amplification). Primers specific for the hPDE IV-B2 isoform gave the identically sized fragment as predicted from the cDNA (data not shown), indicating that at least with respect to the putative splice junction at −23 bp, this is the unspliced genomic sequence. Indeed, examination of the sequence of hPDE IV-B2 at this location (underlined bp −33 to −24 in FIGS. 2 and 3) reveals an excellent match for a splice acceptor sequence (Breathnach R and Chambon P, *Ann. Rev. Biochem.* 50:349 [1981]).

hPDE IV-B is very similar to one of the known rat isozymes, DPD (Colicelli J, et al., *Proc. Nat. Acad. Sci.* (USA) 86:3599 [1989]), with 96.3% amino acid identity in the regions that can be aligned, as compared to only a 74.6% identity with hPDE IV-A. However, of the three splice variants, only hPDE IV-B1 continues to have homology to rat DPD 5' of the putative splice junction (FIG. 4). Indeed, hPDE IV-B1 extends much further 5' than rat DPD, and the homology between the two continues to the 5' end of rat DPD. The fact that the hPDE IV-B1 sequence has been conserved in evolution is strong evidence that this sequence is functional and is translated into protein in vivo. We cannot be sure that the other two splice variants are functional in vivo, although the recent paper (McLaughlin MM et al., *J. Biol. Chem.* 268:6470 [1993]) reporting the hPDE IV-B2 sequence has shown by expression cloning that this isoform can produce enzymatically active protein in a yeast expression system.

Mammalian Expression Clones for hPDE IV-B1, -B2, -B3: The hPDE IV-B1, -B2, -B3 cDNA sequences were subcloned into the mammalian expression vector pcDNA1-amp, a vector that is suitable for transiently expressing these genes in COS cells and that was constructed by replacing the 950 bp NheI fragment of pcDNA1 (Invitrogen) with a 1.2 kb PCR fragment from pUC18 (Sigma) containing the Amp resistance gene. The resulting expression clones are designated pc-hPDE IV-B1, pc-hPDE IV-B2, and pc-hPDE IV-B3. All three clones have been shown to direct the expression of proteins that catalyze the degradation of cAMP when transiently transfected into COS cells.

Genomic Sequences for hPDE IV-B: Overlapping genomic clones define ⁻26 kb of genomic sequence encoding at least the 3' half of the hPDE IV-B gene (FIG. 5). Limited DNA sequencing of these genomic clones confirms that the SalI restriction site in clone λK2.1 is contained in an exon, and corresponds to the unique SalI site seen in the cDNA sequence (1,235–1,240 in Sequence ID No. 1). Hybridization data (FIG. 5) defines the orientation of the gene, and confirms the hybridizing fragment sizes seen in genomic Southern blots hybridized at high stringency with the 308 bp PCR fragment (bp 1,575–1,882 in SECUENCE ID NO. 1) from hPDE IV-B: EcoRI-6.6 kb, HindIII-4.4 kb, BamHI-4.2 kb.

Deposits

Three cDNA clones (pc-hPDE IV-B1, pc-hPDE IV-B2, and pc-hPDE IV-B3) ar being deposited with the American Type Culture Collection, Rockville, Md. U.S.A. (ATCC).

Assays

Using the DNA sequence of hPDE IV-B and hPDE IV-A, one could make a larg number of isoenzyme specific PCR primer pairs. We have made and tested the following hPDE IV-B and hPDE IV-A specific primer pairs. The sequences 5'B(5'-CGAAGAAAGTTACAAGTTC-3') and 3'B(5'-AACCTGGGATTTTTCCACA-3') are a pair of 19-mer primers that specifically amplify a 245 bp fragment from hPDE IV-8, and the sequences 5'A(5'-CACCTGCATCAT-GTACATG-3') and 3'A(5'-TCCCGGTTGTCCTCCAAAG-3') are 19-mers that amplify an 850 bp fragment specifically from hPDE IV-A. In addition, one skilled in the art could easily design a pair of PCR primers specific for each of the hPDE IV-B splice variants by using the unique 5' sequences. Using these primers, one can sensitively assay the presence of these isozymes in any tissue from which total RNA can be isolated (e.g., by the method of Chomcynski P and N Sacchi, *Anal. Biochem.* 162:156 1987) by performing an RT-PCR reaction on such total RNA using the specific primers and then assaying the amount of the appropriately sized DNA PCR product by agarose gel electrophoresis. The RT-PCR conditions are identical to those described in Materials and Methods, except that the thermocycling parameters are as follows: Denature-94° C., 30 sec; Anneal-55° C. 30 sec; Polymerize-72° C., 60. Amplify for at least 30 cycles.

The claimed DNA sequences of this invention can be reproduced by one skilled in the art by either PCR amplification of the coding region using PCR primers designed from the sequences or by obtaining the described cDNA clones from ATCC directly.

Utility of the Invention

A general utility of the novel human PDE IV genes and their encoded peptides is to allow screening for human PDE IV isozyme specific/selective drugs that may b improved therapeutics in the areas of asthma and inflammation. The cloned genes make it possible, by expression cloning methods familiar to those skilled in the art, to produce active, purified isoenzymes that can be used in PDE IV activity assays (e.g., Davis C W, and Daly J W, *J. Cyclic Nucleotide Res.* 5:65 [1979], Torphy TJ and Cielinski L B, *Mol. Pharm.* 37:206 [1990]) to measure the potency of inhibitors against individual isoenzymes. This is true both for distinguishing hPDE IV-A and hPDE IV-B selectiv inhibitors and for distinguishing inhibitors selective between hPDE IV-B1, hPDE IV-B2, or hPDE IV-B3. Since the hPDE IV-B splice variants may each have their own tissue distribution and may be pharmacologically separable from each other, it may be valuable to screen for inhibitors specific for individual splice variants.

Genomic sequences are also of utility in the context of drug discovery. It may be valuable to inhibit the mRNA transcription of a particular isoform rather than to inhibit its translated protein. This is particularly true with hPDE IV-B, since the different splice variants may be transcribed from different promoters. There is precedent for multiple promoters directing the transcription of a mouse brain 2',3'-cyclic-nucleotide 3' phosphodiesterase (Kurihara T et al., *Biochem. Biophys. Res. Comm.* 170:1074 [1990]). This invention would provide the means for one skilled in the art to locate multiple promoters. Isolation of genomic clones containing the promoter(s) and the 5'-most exons of hPDE IV-B1, hPDE IV-B2, and hPDE IV-B3 may be accomplished by screening a human genomic library with the unique 5' sequences. Such promoters could then be linked to a convenient reporter gene such as firefly luciferase (de Wet J R et al., *Mol. Cell. Biol.* 7:725 [1987]), transfected into a mammalian cell line, and used to screen for agents that inhibit the activity of the promoter of interest while having minimal effect on other promoters.

Another utility of the invention is that the DNA sequences, once known, give the information needed to design assays to specifically detect each isoenzyme or splice variant. Isozyme-specific PCR primer pairs are but one example of an assay that depends completely on the knowledge of the specific DNA sequence of the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific hPDE IV isozymes are shown to associated with a particular disease state, the invention would be valuable in the design of diagnostic assays to detect the presence of isozyme mRNA.

Materials and Methods (a) Cells/Reagents

Cells from a human bronchoalveolar lavage (BAL) were purchased from the Johns Hopkins University (Dr. M. Liu). Human brainstem tissue was purchased from the International Institute for the Advancement of Medicine. Unless noted below, all restriction endonucleases and DNA modifying enzymes were from Boehringer-Mannheim.

(b) Degenerate RT-PCR

Total RNA was isolated from human tissue as previously described (Chomcynski P and Sacchi N, *Anal. Biochem.* 162:156 [1987]). To prepare an 80 µl reverse transcriptase (RT) reaction, 4 µg total RNA and 4 µg random hexamer primers (Pharmacia/LKB) were heated to 90° C. for 5 min in 60 µl RNase free water. After chilling on ice, the reaction was brought to 80 µl and the following conditions by the addition of concentrated stocks: 1×RT buffer (50 mM Tris pH 8.3, 6 mM magnesium chloride, 40 mM KCl); 1 mM each dATP, dGTP, dCTP, and dTTP; 1 mM dithiothreitol; 25 U/ml RNasin (Promega); and 900 U/ml AMV reverse transcriptase (RT). Incubate at 42 C for 1 hour, then boil for 5 minutes to inactivate the RT.

A 50 µl PCR reaction was set up by using 3.25 µl of the above reaction mix. Final buffer conditions were (including carryover from RT): 10 mM Tris pH 8.3, 50 mM potassium chloride, 1.5 µM magnesium chloride, 10 µg/ml bovine serum albumin, 2.5% (v/v) Formamide, 200 µM each dNTP, 0.5 pmol/µl each degenerate primer (5'-Deg=5'-CAGGATC-CAAPACNATGGTNGAPAC-3',3'-Deg=5'-GCTCTA-GATCNGCCCANGTYTCCCA-3', where N=A, G, C, or T, P=A or G and Y=C or T) and 0.05 U/µl Amplitaq polymerase (Perkin Elmer). Amplification was don in a Perkin Elmer 9600 PCR thermocycler using the following parameters: denature-94° C., 30 sec; anneal-37° C.+0.5° C./cycle, 60 sec+1 sec/cycle; polymerize-72 C, 60 sec. Amplify for 35 cycles.

(c) Library Screening $8 \times 10^5$ clones from a commercially available human medulla cDNA library (Clontech # HL 1089a) were screened with an 857 bp DNA fragment containing the entire conserved catalytic domain of hPDE IV-A. This fragment was generated by RT-PCR amplification from the Jurkat T-cell line mRNA using unique primers to amplify bp 573–1430 from the PDE IV-A sequence (Uvi GP, et al., *Mol. Cell. Bio.*, 10:2678 [1990]). The fragment was labeled to a specific activity >$5 \times 10^8$ cpm/µg, and hybridized und r the following conditions: 6×SSC, 5× Denhardt's Solution (1× Denhardt's=0.02% each of Ficoll, polyvinylpyrrolidone, and bovine serum albumin), 0.1% sodium dodecyl sulfate (SDS), 100 µg/ml yeast tRNA. Probe concentration was $4 \times 10^6$ cpm/ml. Filters w r hybridized at 65° C. for >16 hours, and then washed to a final stringency of 1×SSC at 55° C.

$1 \times 10^6$ clones from a commercially available human genomic library (Clontech #HL1111j) were screened with the 308 bp PCR fragment of hPDE IV-B (bp 1,575 to 1,882 in SEQUENCE ID NO. 1) and the homologous fragment from hPDE IV-A. The screening conditions were as follows: 5×SSC, 5× Denhardts solution (see above), 40% formamide, 0.5% sodium dodecyl sulfate, and 20 µg/ml herring sperm DNA. Probe concentration was $4 \times 10^5$ cpm/ml. The filters were hybridized at 42° C. for >16 hours, and then washed to a final stringency of 0.5×SSC at room temperature. A genomic library was also constructed in the vector LambdaGEM12 (Promega) using the XhoI half-site method, and $1 \times 10^6$ clones screened under the same hybridization conditions used for the previous genomic library.

(d) DNA Sequencing

All DNA sequencing was done using an ABI model 373A DNA sequencer on DNA fragments cloned into various pGEM vectors (Promega). Sequencing reactions were done using the Taq sequencing method.

(e) RACE Method

The RACE method (Rapid Amplification of cDNA Ends) was adapted from a published method (Frohman MA and Martin GR, In: *Technicue—a Journal of Methods in Cell and Molecular Biology*, Vol. 1, No. 3, pp. 165–170 [1989]). In order to produce the 5' end of the cDNA, an RT reaction was performed on human brainstem total RNA as above with the exception that the gene specific RT primer (GS-RT: 5'-GCAAGTTCTGAATTTGT-3') was at a concentration of 0.1 pmol/µl. The reaction was incubated at 42° C. for 1 hour and then shifted to 52° C. for 30 min. This higher temperature seems to be critical to avoiding a premature truncation product presumably caused by a sequence that AMV RT has difficulty reading through.

After removing buffers using a Centricon 30 filtration device and concentrating in a speedvac, one tails the cDNA with dATP using terminal transferase (TdT) in a 20 µl reaction volume. Final conditions are: 1×TdT buffer (40 mM K-Cacodylate pH 6.8, 0.1 mM dithiothreitol), 0.75 mM $CoCl_2$, 0.2 mM dATP, 1,250 U TdT/ml. Incubate 37° C. for 5 min, inactivate TdT at 65° C. 5 min. This reaction is diluted with water to 500 µl and used as a template in a series of nested PCR reactions.

The first PCR amplification (50 ml) uses the same PCR buffer conditions as above, but uses three primers: the Primer/Adaptor (Ro-d$T_{17}$: 5'-AAGCATCCGTCAG-CATCGGCAGGACAAC($T_{17}$)-3') at 0.2 pmol/µl, the Forward Outside Primer (Ro: 5'-AAGCATCCGTCAGCATC-3') at 0.5 pmol/µl, and the Gene-Specific Reverse Outside Primer (GSo: 5'-ATGGCAGCCAGGATTTC-3') at 0.5 pmol/µl. Taq DNA polymerase is only added after denaturing the reaction to 95° C. for 5 min and equilibrating to 72° C. For the first cycle, the annealing step is 10 min at 55° C., and the extension is at 72° C. for 40 min. After that, cycling parameters (PE 9600 machine) ar: Denature 94° C., 30 sec; Anneal 53° C., 30 sec; Polymerize 72° C., 45 sec. Amplify 28 cycles. Dilute this product 20× to serve as template for a second PCR reaction using primers nested just inside those used in the first PCR reaction. This greatly increases the specificity of the final PCR products.

The second 50 µl PCR reaction uses identical buffer conditions to the first, and uses 1 µl of the 20× diluted product from the first PCR reaction as template DNA. The primers are the Forward Inside Primer (Ri: AGCATCG-GCAGGACAAC-3') and Gene-Specific Inside Primer (GSi: 5'-GGTCGACTGGGCTACAT-3') both at 0.5 pmol/µl. For 12 cycles, the parameters are the same as the final 28 cycles of the previous amplification. The annealing temperature is then raised to 60° C. for another 18 cycles. Products are then analyzed on an agarose gel. They should extend from the GSi primer to the 5' end of the mRNA(s).

Sequence ID Summary
1. hPDE IV-B1 cDNA sequence. 2,554 bp.
2. hPDE IV-B2 cDNA sequence. 2,246 bp.
3. hPDE IV-B3 cDNA sequence. 2,045 bp.
4. Predicted amino acid sequence of hPDE IV-B1. 721 amino acids.
5. Predicted amino acid sequence of hPDE IV-B2. 564 amino acids.
6. Predicted amino acid sequence of hPDE IV-B3. 517 amino acids.

The invention claimed is:

1. An isolated polypeptide comprising the amino acid sequence of one of SEQUENCE ID NO:4, SEQUENCE ID NO:5 or SEQUENCE ID NO:6.

2. A polypeptide produced by expression in a host cell into which has been incorporated the DNA sequence of:
   (a) SEQUENCE ID NO:1
   (b) SEQUENCE ID NO:2 or
   (c) SEQUENCE ID NO:3.

3. An isolated polypeptide of claim 1 comprising the amino acid sequence of SEQ ID NO: b 4.

4. An isolated polypeptide of claim 1 comprising the amino acid sequence of SEQ ID NO:5.

5. An isolated polypeptide of claim 1 comprising the amino acid sequence of SEQ ID NO:6.

6. A recombinant phosphodiesterase encoding a polypeptide, said polypeptide comprising; the amino acid sequence of one of SEQ ID NO:4, SEQ ID NO:5 or SEQ ID NO:6.

7. A polypeptide according to claim 3 comprising the amino acid sequence of SEQ ID NO:4.

8. A polypeptide according to claim 6 comprising the amino acid sequence of SEQ ID NO:5.

9. A polypeptide according to claim 6 comprising the amino acid sequence of SEQ ID NO:6.

10. An isolated polypeptide comprising:
   (a) an amino acid sequence of one of SEQ ID NO:4, SEQ ID NO:5, SEQ ID NO:6 and;
   (b) an amino acid sequence having at least 96.3% sequence identity to one of SEQ ID NO:4, and wherein said amino acid sequence has phosphodiesterase activity.

* * * * *

```
                       SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 2554 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 1:

TGGATGGTGA AAGCTAGCAC TCCTTACAAG ATATGACAGC AAAAGATTCT TCAAAGGAAC        60

TTACTGCTTC TGAACCTGAG GTTTGCATAA AGACTTTCAA GGAGCAAATG CATTTAGAAC       120

TTGAGCTTCC GAGATTACCA GGAAACAGAC CTACATCTCC TAAAATTTCT CCACGCAGTT      180

CACCAAGGAA CTCACCATGC TTTTTCAGAA AGTTGCTGGT GAATAAAAGC ATTCGGCAGC      240

GTCGTCGCTT CACTGTGGCT CATACATGCT TTGATGTGGA AAATGGCCCT TCCCCAGGTC      300

GGAGTCCACT GGATCCCCAG GCCAGCTCTT CCGCTGGGCT GGTACTTCAC GCCACCTTTC      360

CTGGGCACAG CCAGCGCAGA GAGTCATTTC TCTACAGATC AGACAGCGAC TATGACTTGT      420

CACCAAAGGC GATGTCGAGA AACTCTTCTC TTCCAAGCGA GCAACACGGC GATGACTTGA      480

TTGTAACTCC TTTTGCCCAG GTCCTTGCCA GCTTGCGAAG TGTGAGAAAC AACTTCACTA      540
```

```
TACTGACAAA CCTTCATGGT ACATCTAACA AGAGGTCCCC AGCTGCTAGT CAGCCTCCTG        600

TCTCCAGAGT CAACCCACAA GAAGAATCTT ATCAAAAATT AGCAATGGAA ACGCTGGAGG        660

AATTAGACTG GTGTTTAGAC CAGCTAGAGA CCATACAGAC CTACCGGTCT GTCAGTGAGA        720

TGGCTTCTAA CAAGTTCAAA AGAATGCTGA ACCGGGAGCT GACACACCTC TCAGAGATGA        780

GCCGATCAGG GAACCAGGTG TCTGAATACA TTTCAAATAC TTTCTTAGAC AAGCAGAATG        840

ATGTGGAGAT CCCATCTCCT ACCCAGAAAG ACAGGGAGAA AAAGAAAAAG CAGCAGCTCA        900

TGACCCAGAT AAGTGGAGTG AAGAAATTAA TGCATAGTTC AAGCCTAAAC AATACAAGCA        960

TCTCACGCTT TGGAGTCAAC ACTGAAAATG AAGATCACCT GGCCAAGGAG CTGGAAGACC       1020

TGAACAAATG GGGTCTTAAC ATCTTTAATG TGGCTGGATA TTCTCACAAT AGACCCCTAA       1080

CATGCATCAT GTATGCTATA TTCCAGGAAA GAGACCTCCT AAAGACATTC AGAATCTCAT       1140

CTGACACATT TATAACCTAC ATGATGACTT TAGAAGACCA TTACCATTCT GACGTGGCAT       1200

ATCACAACAG CCTGCACGCT GCTGATGTAG CCCAGTCGAC CCATGTTCTC CTTTCTACAC       1260

CAGCATTAGA CGCTGTCTTC ACAGATTTGG AAATCCTGGC TGCCATTTTT GCAGCTGCCA       1320

TCCATGACGT TGATCATCCT GGAGTCTCCA ATCAGTTTCT CATCAACACA AATTCAGAAC       1380

TTGCTTTGAT GTATAATGAT GAATCTGTGT TGGAAAATCA TCACCTTGCT GTGGGTTTCA       1440

AACTGCTGCA AGGAGAACAC TGTGACATCT TCATGAATCT CACCAAGAAG CAGCGTCAGA       1500

CACTCAGGAA GATGGTTATT GACATGGTGT TAGCAACTGA TATGTCTAAA CATATGAGCC       1560

TGCTGGCAGA CCTGAAGACA ATGGTAGAAA CGAAGAAAGT TACAAGTTCA GGCGTTCTTC       1620

TCCTAGACAA CTATACCGAT CGCATTCAGG TCCTTCGCAA CATGGTACAC TGTGCAGACC       1680

TGAGCAACCC CACCAAGTCC TTGGAATTGT ATCGGCAATG GACAGACCGC TCATGGAGG        1740

AATTTTTCCA GCAGGGAGAC AAAGAGCGGG AGAGGGAAT GGAAATTAGC CCAATGTGTG        1800

ATAAACACAC AGCTTCTGTG GAAAAATCCC AGGTTGGTTT CATCGACTAC ATTGTCCATC       1860

CATTGTGGGA GACATGGGCA GATTTGGTAC AGCCTGATGC TCAGGACATT CTCGATACCT       1920

TAGAAGATAA CAGGAACTGG TATCAGAGCA TGATACCTCA AAGTCCCTCA CCACCACTGG       1980

ACGAGCAGAA CAGGGACTGC CAGGGTCTGA TGGAGAAGTT TCAGTTTGAA CTGACTCTCG       2040

ATGAGGAAGA TTCTGAAGGA CCTGAGAAGG AGGGAGAGGG ACACAGCTAT TTCAGCAGCA       2100

CAAAGACGCT TTGTGTGATT GATCCAGAAA ACAGAGATTC CCTGGGAGAG ACTGACATAG       2160

ACATTGCAAC AGAAGACAAG TCCCCCGTGG ATACATAATC CCCCTCTCCC TGTGGAGATG       2220

AACATTCTAT CCTTGATGAG CATGCCAGCT ATGTGGTAGG GCCAGCCCAC CATGGGGCC        2280

AAGACCTGCA CAGGACAAGG GCCACCTGGC CTTTCAGTTA CTTGAGTTTG GAGTCAGAAA       2340

GCAAGACCAG GAAGCAAATA GCAGCTCAGG AAATCCCACG GTTGACTTGC CTTGATGGCA       2400

AGCTTGGTGG AGAGGACTGA AGCTGTTGCT GGGGGCCGAT TCTGATCAAG ACACATGGCT       2460

TGTAAATGGA AGACACAACA CTGAGAGATC ATTCTGCTCT AAGTTTCGGG AACTTATCCC       2520

CGACAGTGAC TGAACTCACT GACTAATAAC TTCC                                  2554
```

(2) INFORMATION FOR SEQ ID NO: 2:

(i) SEQUENCE CHARACTERISTICS:
        (A) LENGTH: 2246 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

```
CATTTATGCA GATGAGCTTA TAAGAGACCG TTCCCTCCGC CTTCTTCCTC AGAGGAAGTT        60

TCTTGGTAGA TCACCGACAC CTCATCCAGG CGGGGGGTTG GGGGGAAACT TGGCACCAGC       120

CATCCCAGGC AGAGCACCAC TGTGATTTGT TCTCCTGGTG GAGAGAGCTG GAAGGAAGGA       180

GCCAGCGTCC AAATAATGAA GGAGCACGGG GGCACCTTCA GTAGCACCGG AATCAGCGGT       240

GGTACGGGTG ACTCTGCTAT GGACAGCCTG CAGCCGCTCC AGCCTAACTA CATGCCTGTG       300

TGTTTGTTTG CAGAAGAATC TTATCAAAAA TTAGCAATGG AAACGCTGGA GGAATTAGAC       360

TGGTGTTTAG ACCAGCTAGA GACCATACAG ACCTACCGGT CTGTCAGTGA GATGGCTTCT       420

AACAAGTTCA AAAGAATGCT GAACCGGGAG CTGACACACC TCTCAGAGAT GAGCCGATCA       480

GGGAACCAGG TGTCTGAATA CATTTCAAAT ACTTTCTTAG ACAAGCAGAA TGATGTGGAG       540

ATCCCATCTC CTACCCAGAA AGACAGGGAG AAAAAGAAAA AGCAGCAGCT CATGACCCAG       600

ATAAGTGGAG TGAAGAAATT AATGCATAGT TCAAGCCTAA ACAATACAAG CATCTCACGC       660

TTTGGAGTCA ACACTGAAAA TGAAGATCAC CTGGCCAAGG AGCTGGAAGA CCTGAACAAA       720

TGGGGTCTTA ACATCTTTAA TGTGGCTGGA TATTCTCACA ATAGACCCCT AACATGCATC       780

ATGTATGCTA TATTCCAGGA AAGAGACCTC CTAAAGACAT TCAGAATCTC ATCTGACACA       840

TTTATAACCT ACATGATGAC TTTAGAAGAC CATTACCATT CTGACGTGGC ATATCACAAC       900

AGCCTGCACG CTGCTGATGT AGCCCAGTCG ACCCATGTTC TCCTTTCTAC ACCAGCATTA       960

GACGCTGTCT TCACAGATTT GGAAATCCTG GCTGCCATTT TTGCAGCTGC CATCCATGAC      1020

GTTGATCATC CTGGAGTCTC CAATCAGTTT CTCATCAACA CAAATTCAGA ACTTGCTTTG      1080

ATGTATAATG ATGAATCTGT GTTGGAAAAT CATCACCTTG CTGTGGGTTT CAAACTGCTG      1140

CAAGGAGAAC ACTGTGACAT CTTCATGAAT CTCACCAAGA AGCAGCGTCA GACACTCAGG      1200

AAGATGGTTA TTGACATGGT GTTAGCAACT GATATGTCTA AACATATGAG CCTGCTGGCA      1260

GACCTGAAGA CAATGGTAGA AACGAAGAAA GTTACAAGTT CAGGCGTTCT TCTCCTAGAC      1320

AACTATACCG ATCGCATTCA GGTCCTTCGC AACATGGTAC ACTGTGCAGA CCTGAGCAAC      1380

CCCACCAAGT CCTTGGAATT GTATCGGCAA TGGACAGACC GCCTCATGGA GGAATTTTTC      1440

CAGCAGGGAG ACAAAGAGCG GGAGAGGGGA ATGGAAATTA GCCCAATGTG TGATAAACAC      1500

ACAGCTTCTG TGGAAAAATC CCAGGTTGGT TTCATCGACT ACATTGTCCA TCCATTGTGG      1560

GAGACATGGG CAGATTTGGT ACAGCCTGAT GCTCAGGACA TTCTCGATAC CTTAGAAGAT      1620

AACAGGAACT GGTATCAGAG CATGATACCT CAAAGTCCCT CACCACCACT GGACGAGCAG      1680

AACAGGGACT GCCAGGGTCT GATGGAGAAG TTTCAGTTTG AACTGACTCT CGATGAGGAA      1740

GATTCTGAAG GACCTGAGAA GGAGGGAGAG GGACACAGCT ATTTCAGCAG CACAAAGACG      1800

CTTTGTGTGA TTGATCCAGA AAACAGAGAT TCCCTGGGAG AGACTGACAT AGACATTGCA      1860

ACAGAAGACA AGTCCCCCGT GGATACATAA TCCCCCTCTC CCTGTGGAGA TGAACATTCT      1920

ATCCTTGATG AGCATGCCAG CTATGTGGTA GGGCCAGCCC ACCATGGGGG CCAAGACCTG      1980

CACAGGACAA GGGCCACCTG GCCTTTCAGT TACTTGAGTT TGGAGTCAGA AAGCAAGACC      2040

AGGAAGCAAA TAGCAGCTCA GGAAATCCCA CGGTTGACTT GCCTTGATGG CAAGCTTGGT      2100

GGAGAGGACT GAAGCTGTTG CTGGGGGCCG ATTCTGATCA AGACACATGG CTTGTAAATG      2160

GAAGACACAA CACTGAGAGA TCATTCTGCT CTAAGTTTCG GGAACTTATC CCCGACAGTG      2220

ACTGAACTCA CTGACTAATA ACTTCC                                          2246
```

(2) INFORMATION FOR SEQ ID NO: 3:

(i) SEQUENCE CHARACTERISTICS:
        (A) LENGTH: 2045 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

```
GTGGAAGCAA ACAGCGGAGG CAAGGGGTTG TTTCGGACAC ACTAGAGAGT AAGTCAGAGA      60
ATCTTCGTGT TGAGGCAGCA TTGCAAAATT GAAGATGAAG AAAGGAAGGA AGAAGAATCT     120
TATCAAAAAT TAGCAATGGA AACGCTGGAG GAATTAGACT GGTGTTTAGA CCAGCTAGAG     180
ACCATACAGA CCTACCGGTC TGTCAGTGAG ATGGCTTCTA ACAAGTTCAA AAGAATGCTG     240
AACCGGGAGC TGACACACCT CTCAGAGATG AGCCGATCAG GGAACCAGGT GTCTGAATAC     300
ATTTCAAATA CTTTCTTAGA CAAGCAGAAT GATGTGGAGA TCCCATCTCC TACCCAGAAA     360
GACAGGGAGA AAAAGAAAAA GCAGCAGCTC ATGACCCAGA TAAGTGGAGT GAAGAAATTA     420
ATGCATAGTT CAAGCCTAAA CAATACAAGC ATCTCACGCT TTGGAGTCAA CACTGAAAAT     480
GAAGATCACC TGGCCAAGGA GCTGGAAGAC CTGAACAAAT GGGGTCTTAA CATCTTTAAT     540
GTGGCTGGAT ATTCTCACAA TAGACCCCTA ACATGCATCA TGTATGCTAT ATTCCAGGAA     600
AGAGACCTCC TAAAGACATT CAGAATCTCA TCTGACACAT TTATAACCTA CATGATGACT     660
TTAGAAGACC ATTACCATTC TGACGTGGCA TATCACAACA GCCTGCACGC TGCTGATGTA     720
GCCCAGTCGA CCCATGTTCT CCTTTCTACA CCAGCATTAG ACGCTGTCTT CACAGATTTG     780
GAAATCCTGG CTGCCATTTT TGCAGCTGCC ATCCATGACG TTGATCATCC TGGAGTCTCC     840
AATCAGTTTC TCATCAACAC AAATTCAGAA CTTGCTTTGA TGTATAATGA TGAATCTGTG     900
TTGGAAAATC ATCACCTTGC TGTGGGTTTC AAACTGCTGC AAGGAGAACA CTGTGACATC     960
TTCATGAATC TCACCAAGAA GCAGCGTCAG ACACTCAGGA AGATGGTTAT TGACATGGTG    1020
TTAGCAACTG ATATGTCTAA ACATATGAGC CTGCTGGCAG ACCTGAAGAC AATGGTAGAA    1080
ACGAAGAAAG TTACAAGTTC AGGCGTTCTT CTCCTAGACA ACTATACCGA TCGCATTCAG    1140
GTCCTTCGCA ACATGGTACA CTGTGCAGAC CTGAGCAACC CCACCAAGTC CTTGGAATTG    1200
TATCGGCAAT GGACAGACCG CCTCATGGAG GAATTTTTCC AGCAGGGAGA CAAAGAGCGG    1260
GAGAGGGGAA TGGAAATTAG CCCAATGTGT GATAAACACA CAGCTTCTGT GGAAAAATCC    1320
CAGGTTGGTT TCATCGACTA CATTGTCCAT CCATTGTGGG AGACATGGGC AGATTTGGTA    1380
CAGCCTGATG CTCAGGACAT TCTCGATACC TTAGAAGATA ACAGGAACTG GTATCAGAGC    1440
ATGATACCTC AAAGTCCCTC ACCACCACTG GACGAGCAGA ACAGGGACTG CCAGGGTCTG    1500
ATGGAGAAGT TTCAGTTTGA ACTGACTCTC GATGAGGAAG ATTCTGAAGG ACCTGAGAAG    1560
GAGGGAGAGG GACACAGCTA TTTCAGCAGC ACAAAGACGC TTTGTGTGAT TGATCCAGAA    1620
AACAGAGATT CCCTGGGAGA GACTGACATA GACATTGCAA CAGAAGACAA GTCCCCCGTG    1680
GATACATAAT CCCCCTCTCC CTGTGGAGAT GAACATTCTA TCCTTGATGA GCATGCCAGC    1740
TATGTGGTAG GGCCAGCCCA CCATGGGGGC CAAGACCTGC ACAGGACAAG GCCACCTGG     1800
CCTTTCAGTT ACTTGAGTTT GGAGTCAGAA AGCAAGACCA GGAAGCAAAT AGCAGCTCAG    1860
GAAATCCCAC GGTTGACTTG CCTTGATGGC AAGCTTGGTG GAGAGGACTG AAGCTGTTGC    1920
TGGGGGCCGA TTCTGATCAA GACACATGGC TTGTAAATGG AAGACACAAC ACTGAGAGAT    1980
CATTCTGCTC TAAGTTTCGG GAACTTATCC CCGACAGTGA CTGAACTCAC TGACTAATAA    2040
```

```
CTTCC                                                              2045
```

(2) INFORMATION FOR SEQ ID NO: 4:

(i) SEQUENCE CHARACTERISTICS:
        (A) LENGTH: 721 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Met Thr Ala Lys Asp Ser Ser Lys Glu Leu Thr Ala Ser Glu Pro Glu
1               5                  10                  15

Val Cys Ile Lys Thr Phe Lys Glu Gln Met His Leu Glu Leu Glu Leu
            20                  25                  30

Pro Arg Leu Pro Gly Asn Arg Pro Thr Ser Pro Lys Ile Ser Pro Arg
        35                  40                  45

Ser Ser Pro Arg Asn Ser Pro Cys Phe Phe Arg Lys Leu Leu Val Asn
50                  55                  60

Lys Ser Ile Arg Gln Arg Arg Phe Thr Val Ala His Thr Cys Phe
65                  70                  75                  80

Asp Val Glu Asn Gly Pro Ser Pro Gly Arg Ser Pro Leu Asp Pro Gln
                85                  90                  95

Ala Ser Ser Ser Ala Gly Leu Val Leu His Ala Thr Phe Pro Gly His
            100                 105                 110

Ser Gln Arg Arg Glu Ser Phe Leu Tyr Arg Ser Asp Ser Asp Tyr Asp
        115                 120                 125

Leu Ser Pro Lys Ala Met Ser Arg Asn Ser Ser Leu Pro Ser Glu Gln
130                 135                 140

His Gly Asp Asp Leu Ile Val Thr Pro Phe Ala Gln Val Leu Ala Ser
145                 150                 155                 160

Leu Arg Ser Val Arg Asn Asn Phe Thr Ile Leu Thr Asn Leu His Gly
                165                 170                 175

Thr Ser Asn Lys Arg Ser Pro Ala Ala Ser Gln Pro Pro Val Ser Arg
            180                 185                 190

Val Asn Pro Gln Glu Ser Tyr Gln Lys Leu Ala Met Glu Thr Leu
        195                 200                 205

Glu Glu Leu Asp Trp Cys Leu Asp Gln Leu Glu Thr Ile Gln Thr Tyr
210                 215                 220

Arg Ser Val Ser Glu Met Ala Ser Asn Lys Phe Lys Arg Met Leu Asn
225                 230                 235                 240

Arg Glu Leu Thr His Leu Ser Glu Met Ser Arg Ser Gly Asn Gln Val
                245                 250                 255

Ser Glu Tyr Ile Ser Asn Thr Phe Leu Asp Lys Gln Asn Asp Val Glu
            260                 265                 270

Ile Pro Ser Pro Thr Gln Lys Asp Arg Glu Lys Lys Lys Gln Gln
        275                 280                 285

Leu Met Thr Gln Ile Ser Gly Val Lys Lys Leu Met His Ser Ser Ser
290                 295                 300

Leu Asn Asn Thr Ser Ile Ser Arg Phe Gly Val Asn Thr Glu Asn Glu
305                 310                 315                 320

Asp His Leu Ala Lys Glu Leu Glu Asp Leu Asn Lys Trp Gly Leu Asn
                325                 330                 335
```

-continued

```
Ile Phe Asn Val Ala Gly Tyr Ser His Asn Arg Pro Leu Thr Cys Ile
            340                 345                 350

Met Tyr Ala Ile Phe Gln Glu Arg Asp Leu Leu Lys Thr Phe Arg Ile
            355                 360                 365

Ser Ser Asp Thr Phe Ile Thr Tyr Met Met Thr Leu Glu Asp His Tyr
            370                 375                 380

His Ser Asp Val Ala Tyr His Asn Ser Leu His Ala Ala Asp Val Ala
385                 390                 395                 400

Gln Ser Thr His Val Leu Leu Ser Thr Pro Ala Leu Asp Ala Val Phe
                405                 410                 415

Thr Asp Leu Glu Ile Leu Ala Ala Ile Phe Ala Ala Ala Ile His Asp
                420                 425                 430

Val Asp His Pro Gly Val Ser Asn Gln Phe Leu Ile Asn Thr Asn Ser
                435                 440                 445

Glu Leu Ala Leu Met Tyr Asn Asp Glu Ser Val Leu Glu Asn His His
            450                 455                 460

Leu Ala Val Gly Phe Lys Leu Leu Gln Gly Glu His Cys Asp Ile Phe
465                 470                 475                 480

Met Asn Leu Thr Lys Lys Gln Arg Gln Thr Leu Arg Lys Met Val Ile
                485                 490                 495

Asp Met Val Leu Ala Thr Asp Met Ser Lys His Met Ser Leu Leu Ala
                500                 505                 510

Asp Leu Lys Thr Met Val Glu Thr Lys Lys Val Thr Ser Ser Gly Val
                515                 520                 525

Leu Leu Leu Asp Asn Tyr Thr Asp Arg Ile Gln Val Leu Arg Asn Met
            530                 535                 540

Val His Cys Ala Asp Leu Ser Asn Pro Thr Lys Ser Leu Glu Leu Tyr
545                 550                 555                 560

Arg Gln Trp Thr Asp Arg Leu Met Glu Glu Phe Phe Gln Gln Gly Asp
                565                 570                 575

Lys Glu Arg Glu Arg Gly Met Glu Ile Ser Pro Met Cys Asp Lys His
                580                 585                 590

Thr Ala Ser Val Glu Lys Ser Gln Val Gly Phe Ile Asp Tyr Ile Val
            595                 600                 605

His Pro Leu Trp Glu Thr Trp Ala Asp Leu Val Gln Pro Asp Ala Gln
            610                 615                 620

Asp Ile Leu Asp Thr Leu Glu Asp Asn Arg Asn Trp Tyr Gln Ser Met
625                 630                 635                 640

Ile Pro Gln Ser Pro Ser Pro Pro Leu Asp Glu Gln Asn Arg Asp Cys
                645                 650                 655

Gln Gly Leu Met Glu Lys Phe Gln Phe Glu Leu Thr Leu Asp Glu Glu
                660                 665                 670

Asp Ser Glu Gly Pro Glu Lys Glu Gly Glu Gly His Ser Tyr Phe Ser
                675                 680                 685

Ser Thr Lys Thr Leu Cys Val Ile Asp Pro Glu Asn Arg Asp Ser Leu
            690                 695                 700

Gly Glu Thr Asp Ile Asp Ile Ala Thr Glu Asp Lys Ser Pro Val Asp
705                 710                 715                 720

Thr
```

(2) INFORMATION FOR SEQ ID NO: 5:

(i) SEQUENCE CHARACTERISTICS:
        (A) LENGTH: 564 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Met Lys Glu His Gly Gly Thr Phe Ser Ser Thr Gly Ile Ser Gly
1               5                  10                  15

Ser Gly Asp Ser Ala Met Asp Ser Leu Gln Pro Leu Gln Pro Asn Tyr
            20                  25                  30

Met Pro Val Cys Leu Phe Ala Glu Glu Ser Tyr Gln Lys Leu Ala Met
                35                  40                  45

Glu Thr Leu Glu Glu Leu Asp Trp Cys Leu Asp Gln Leu Glu Thr Ile
50                      55                  60

Gln Thr Tyr Arg Ser Val Ser Glu Met Ala Ser Asn Lys Phe Lys Arg
65                  70                  75                  80

Met Leu Asn Arg Glu Leu Thr His Leu Ser Glu Met Ser Arg Ser Gly
                85                  90                  95

Asn Gln Val Ser Glu Tyr Ile Ser Asn Thr Phe Leu Asp Lys Gln Asn
            100                 105                 110

Asp Val Glu Ile Pro Ser Pro Thr Gln Lys Asp Arg Glu Lys Lys Lys
            115                 120                 125

Lys Gln Gln Leu Met Thr Gln Ile Ser Gly Val Lys Lys Leu Met His
    130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Glu Asp Leu Asn Lys Trp
                165                 170                 175

Gly Leu Asn Ile Phe Asn Val Ala Gly Tyr Ser His Asn Arg Pro Leu
            180                 185                 190

Thr Cys Ile Met Tyr Ala Ile Phe Gln Glu Arg Asp Leu Leu Lys Thr
            195                 200                 205

Phe Arg Ile Ser Ser Asp Thr Phe Ile Thr Tyr Met Met Thr Leu Glu
210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
                245                 250                 255

Ala Val Phe Thr Asp Leu Glu Ile Leu Ala Ala Ile Phe Ala Ala Ala
            260                 265                 270

Ile His Asp Val Asp His Pro Gly Val Ser Asn Gln Phe Leu Ile Asn
            275                 280                 285

Thr Asn Ser Glu Leu Ala Leu Met Tyr Asn Asp Glu Ser Val Leu Glu
290                 295                 300

Asn His His Leu Ala Val Gly Phe Lys Leu Leu Gln Gly Glu His Cys
305                 310                 315                 320

Asp Ile Phe Met Asn Leu Thr Lys Lys Gln Arg Gln Thr Leu Arg Lys
                325                 330                 335

Met Val Ile Asp Met Val Leu Ala Thr Asp Met Ser Lys His Met Ser
            340                 345                 350

Leu Leu Ala Asp Leu Lys Thr Met Val Glu Thr Lys Lys Val Thr Ser
            355                 360                 365

Ser Gly Val Leu Leu Leu Asp Asn Tyr Thr Asp Arg Ile Gln Val Leu
370                 375                 380

-continued

```
Arg Asn Met Val His Cys Ala Asp Leu Ser Asn Pro Thr Lys Ser Leu
385                 390                 395                 400

Glu Leu Tyr Arg Gln Trp Thr Asp Arg Leu Met Glu Phe Phe Gln
        405                 410                 415

Gln Gly Asp Lys Glu Arg Glu Arg Gly Met Glu Ile Ser Pro Met Cys
            420                 425                 430

Asp Lys His Thr Ala Ser Val Glu Lys Ser Gln Val Gly Phe Ile Asp
            435                 440                 445

Tyr Ile Val His Pro Leu Trp Glu Thr Trp Ala Asp Leu Val Gln Pro
450                 455                 460

Asp Ala Gln Asp Ile Leu Asp Thr Leu Glu Asp Asn Arg Asn Trp Tyr
465                 470                 475                 480

Gln Ser Met Ile Pro Gln Ser Pro Ser Pro Leu Asp Glu Gln Asn
                485                 490                 495

Arg Asp Cys Gln Gly Leu Met Glu Lys Phe Gln Phe Glu Leu Thr Leu
            500                 505                 510

Asp Glu Glu Asp Ser Glu Gly Pro Glu Lys Glu Gly Glu Gly His Ser
            515                 520                 525

Tyr Phe Ser Ser Thr Lys Thr Leu Cys Val Ile Asp Pro Glu Asn Arg
530                 535                 540

Asp Ser Leu Gly Glu Thr Asp Ile Asp Ile Ala Thr Glu Asp Lys Ser
545                 550                 555                 560

Pro Val Asp Thr (2) INFORMATION FOR SEQ ID NO: 6:

(i) SEQUENCE CHARACTERISTICS:
        (A) LENGTH: 517 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Met Glu Thr Leu Glu Glu Leu Asp Trp Cys Leu Asp Gln Leu Glu Thr
1               5                   10                  15

Ile Gln Thr Tyr Arg Ser Val Ser Glu Met Ala Ser Asn Lys Phe Lys
            20                  25                  30

Arg Met Leu Asn Arg Glu Leu Thr His Leu Ser Glu Met Ser Arg Ser
        35                  40                  45

Gly Asn Gln Val Ser Glu Tyr Ile Ser Asn Thr Phe Leu Asp Lys Gln
    50                  55                  60

Asn Asp Val Glu Ile Pro Ser Pro Thr Gln Lys Asp Arg Glu Lys Lys
65                  70                  75                  80

Lys Lys Gln Gln Leu Met Thr Gln Ile Ser Gly Val Lys Lys Leu Met
                85                  90                  95

His Ser Ser Ser Leu Asn Asn Thr Ser Ile Ser Arg Phe Gly Val Asn
                100                 105                 110

Thr Glu Asn Glu Asp His Leu Ala Lys Glu Leu Glu Asp Leu Asn Lys
            115                 120                 125

Trp Gly Leu Asn Ile Phe Asn Val Ala Gly Tyr Ser His Asn Arg Pro
        130                 135                 140

Leu Thr Cys Ile Met Tyr Ala Ile Phe Gln Glu Arg Asp Leu Leu Lys
145                 150                 155                 160
```

-continued

```
Thr Phe Arg Ile Ser Ser Asp Thr Phe Ile Thr Tyr Met Met Thr Leu
            165                 170                 175

Glu Asp His Tyr His Ser Asp Val Ala Tyr His Asn Ser Leu His Ala
        180                 185                 190

Ala Asp Val Ala Gln Ser Thr His Val Leu Leu Ser Thr Pro Ala Leu
        195                 200                 205

Asp Ala Val Phe Thr Asp Leu Glu Ile Leu Ala Ala Ile Phe Ala Ala
        210                 215                 220

Ala Ile His Asp Val Asp His Pro Gly Val Ser Asn Gln Phe Leu Ile
225                 230                 235                 240

Asn Thr Asn Ser Glu Leu Ala Leu Met Tyr Asn Asp Glu Ser Val Leu
            245                 250                 255

Glu Asn His His Leu Ala Val Gly Phe Lys Leu Leu Gln Gly Glu His
            260                 265                 270

Cys Asp Ile Phe Met Asn Leu Thr Lys Lys Gln Arg Gln Thr Leu Arg
        275                 280                 285

Lys Met Val Ile Asp Met Val Leu Ala Thr Asp Met Ser Lys His Met
        290                 295                 300

Ser Leu Leu Ala Asp Leu Lys Thr Met Val Glu Thr Lys Lys Val Thr
305                 310                 315                 320

Ser Ser Gly Val Leu Leu Leu Asp Asn Tyr Thr Asp Arg Ile Gln Val
            325                 330                 335

Leu Arg Asn Met Val His Cys Ala Asp Leu Ser Asn Pro Thr Lys Ser
            340                 345                 350

Leu Glu Leu Tyr Arg Gln Trp Thr Asp Arg Leu Met Glu Glu Phe Phe
            355                 360                 365

Gln Gln Gly Asp Lys Glu Arg Glu Arg Gly Met Glu Ile Ser Pro Met
        370                 375                 380

Cys Asp Lys His Thr Ala Ser Val Glu Lys Ser Gln Val Gly Phe Ile
385                 390                 395                 400

Asp Tyr Ile Val His Pro Leu Trp Glu Thr Trp Ala Asp Leu Val Gln
            405                 410                 415

Pro Asp Ala Gln Asp Ile Leu Asp Thr Leu Glu Asp Asn Arg Asn Trp
            420                 425                 430

Tyr Gln Ser Met Ile Pro Gln Ser Pro Ser Pro Leu Asp Glu Gln
            435                 440                 445

Asn Arg Asp Cys Gln Gly Leu Met Glu Lys Phe Gln Phe Glu Leu Thr
            450                 455                 460

Leu Asp Glu Glu Asp Ser Glu Gly Pro Glu Lys Glu Gly Glu Gly His
465                 470                 475                 480

Ser Tyr Phe Ser Ser Thr Lys Thr Leu Cys Val Ile Asp Pro Glu Asn
            485                 490                 495

Arg Asp Ser Leu Gly Glu Thr Asp Ile Asp Ile Ala Thr Glu Asp Lys
            500                 505                 510

Ser Pro Val Asp Thr
            515
```